(12) United States Patent
Gainer et al.

(10) Patent No.: US 8,512,745 B2
(45) Date of Patent: Aug. 20, 2013

(54) ULIPRISTAL ACETATE TABLETS

(75) Inventors: Erin Gainer, Paris (FR); Helene Guillard, Paris (FR); Denis Gicquel, Orgeval (FR); Marianne Henrion, Paris (FR); Céline Gnakamene, Paris (FR)

(73) Assignee: Laboratoire HRA Pharma, Paris (FR)

( * ) Notice: Subject to any disclaimer, the term of this patent is extended or adjusted under 35 U.S.C. 154(b) by 433 days.

(21) Appl. No.: 12/329,865

(22) Filed: Dec. 8, 2008

(65) Prior Publication Data
US 2010/0144692 A1 Jun. 10, 2010

(51) Int. Cl.
*A61K 9/20* (2006.01)
*A61K 31/56* (2006.01)

(52) U.S. Cl.
USPC ............................. 424/464; 514/179

(58) Field of Classification Search
USPC .......................... 424/464; 514/179
See application file for complete search history.

(56) References Cited

U.S. PATENT DOCUMENTS

| | | | |
|---|---|---|---|
| 4,954,490 A | 9/1990 | Cook | |
| 5,073,548 A | 12/1991 | Cook | |
| 5,084,277 A * | 1/1992 | Greco et al. | 424/433 |
| 5,759,577 A * | 6/1998 | Barcomb | 424/479 |
| 5,929,262 A | 7/1999 | Kim | |
| 2007/0213306 A1 * | 9/2007 | Hausknecht | 514/169 |

FOREIGN PATENT DOCUMENTS

| | | |
|---|---|---|
| WO | WO2004/065405 | 8/2004 |
| WO | WO2004/078709 | 9/2004 |
| WO | 2008/067086 | 6/2008 |
| WO | 2008/083192 | 7/2008 |
| WO | 2008/129396 | 10/2008 |

OTHER PUBLICATIONS

Barcomb (US 5,759,577) in view of Bholhuis et al (Pharmaceutical Development and Technology, 11:111-124, 2006).*
Chabbert-Buffet et al (J Clin Endocrinol Metab, Sep. 2007, 92(9):3582-3589).*
Levy et al (Pharmacokinetics of the progesterone-containing vaginal tablet and its use in assisted reproduction, Steroids, vol. 65, Issues 10-11, Oct.-Nov. 2000, pp. 645-6490).*
Levens, et al. "CDB-2914 for Uterine Leiomyomata Treatment a Randomized Controlled Trial," Obstetrics & Gynecology, 2008, vol. 111, No. 5; pp. 1129-1136.
Blithe, et al. "Development of the Selective Progesterone Receptor Modulator CDB-2914 for Clinical Indications," Steroids 2003, 68; pp. 1013-1017.
Creinin, et al. "Progesterone Receptor Modulator for Emergency Contraception a Randomized Controlled Trial," Obstetrics & Gynecology, 2006, vol. 108, No. 5; pp. 1089-1097.
International Search Report and Written Opinion for international application No. PCT/EP2009/066652 issued by the International Searching Authority mailed on Jun. 9, 2010.

* cited by examiner

*Primary Examiner* — Benjamin Packard
(74) *Attorney, Agent, or Firm* — Fahmi, Sellers, Embert & Davitz

(57) ABSTRACT

The invention relates to a pharmaceutical tablet for oral administration comprising ulipristal acetate together with the following excipients: a diluent in an amount of 60 to 95 wt %, a binding agent in an amount of 1 to 10 wt %, croscarmellose sodium in an amount of 1 to 10 wt %, and magnesium stearate in an amount of 0 to 5 wt %.

16 Claims, 1 Drawing Sheet

ULIPRISTAL ACETATE TABLETS

Figure 1:
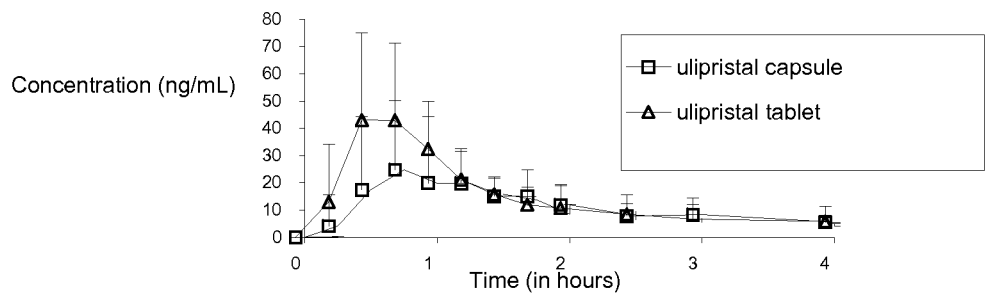

The present invention relates to an ulipristal acetate tablet for oral administration, as well as to the manufacture and uses thereof.

BACKGROUND TO THE INVENTION

Ulipristal acetate, formerly known as CDB-2914, designates within the context of this application 17α-acetoxy-11β-[4-N,N-dimethylamino-phenyl)-19-norpregna-4,9-diene-3,20-dione, represented by formula I:

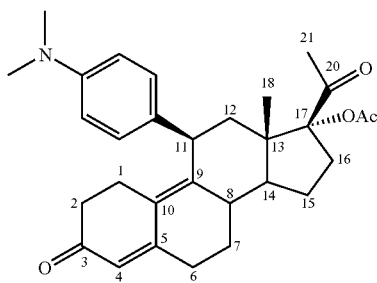

Ulipristal acetate, and methods for its preparation, are described e.g., in U.S. Pat. Nos. 4,954,490; 5,073,548, and 5,929,262, as well as in international patent applications WO2004/065405 and WO2004/078709.

Ulipristal acetate possesses antiprogestational and antiglucocorticoidal activity, and has been proposed for contraception, in particular for emergency contraception, and for the therapy of various hormonal diseases. Properties of this compound are further described in Blithe et al, Steroids. 2003 68(10-13):1013-7. So far, clinical trials have been conducted using oral capsules of ulipristal acetate (Creinin et al, Obstetrics & Gynecology 2006; 108:1089-1097; Levens et al, Obstet Gynecol. 2008, 111(5):1129-36). In order to increase the properties and clinical benefit of this molecule, there is a need for improved formulations thereof.

SUMMARY OF THE INVENTION

The present invention relates to novel formulations of ulipristal acetate. More specifically, the invention relates to particular oral tablets of micronized ulipristal acetate. The inventors have now shown that the bioavailability, and hence the efficiency of ulipristal acetate, can be enhanced when formulating ulipristal acetate as a tablet under particular conditions. More specifically, the inventors have conducted many tests and discovered that the properties of ulipristal acetate can be improved when this compound is formulated as an oral tablet using particular types and amounts of excipients.

Accordingly, the invention relates to a pharmaceutical tablet for oral administration, comprising ulipristal acetate in an amount of 3 to 18 wt %, together with the following excipients: a diluent in an amount of 60 to 95 wt %, a binding agent in an amount of 1 to 10 wt %, croscarmellose sodium in an amount of 1 to 10 wt %, and magnesium stearate in an amount of 0 to 5 wt %.

Surprisingly, the inventors have shown that a micronized ulipristal acetate formulation according to the present invention exhibits not only very good pharmacotechnical characteristics (in particular hardness, friability, stability) for the manufacturing of the tablet, but also provides a substantially improved dissolution profile for ulipristal acetate.

According to preferred embodiments, the formulation comprises 10% wt ulipristal acetate and is designed to contain from 5 to 50 mg ulipristal acetate.

A further object of this invention relates to a method of manufacturing an ulipristal acetate tablet, the method comprising mixing the above ingredients and ulipristal acetate and forming a tablet.

A further object of this invention resides in a method of contraception comprising administering to a subject in need thereof an effective amount of a tablet of this invention.

A further object of this invention resides in a method of treating a hormonal disease, comprising administering to a subject in need thereof an effective amount of a tablet of this invention.

A further object of this invention is an ulipristal acetate tablet as defined above as a contraceptive.

LEGEND TO THE FIGURES

FIG. 1. Mean (±S.D) plasma concentration versus time profiles of Ulipristal acetate on linear and log-linear scale. Comparison of the collected data from the tablet comprising 10 mg ulipristal acetate versus the capsule containing 10 mg ulipristal acetate in 120 mg microcrystalline cellulose.
X-axis: time in hours
Y-axis: Concentration of ulipristal acetate measured in the plasma in ng/mL.
The concentration of ulipristal acetate was measured using liquid chromatography with tandem mass spectrometric detection LC-MS/MS, with a validated calibration range in between 0.100-20.0 ng/mL. The sample was later re-assayed using the non specific radioimmunoassay RIA Bioqual Inc.

Figure 2:
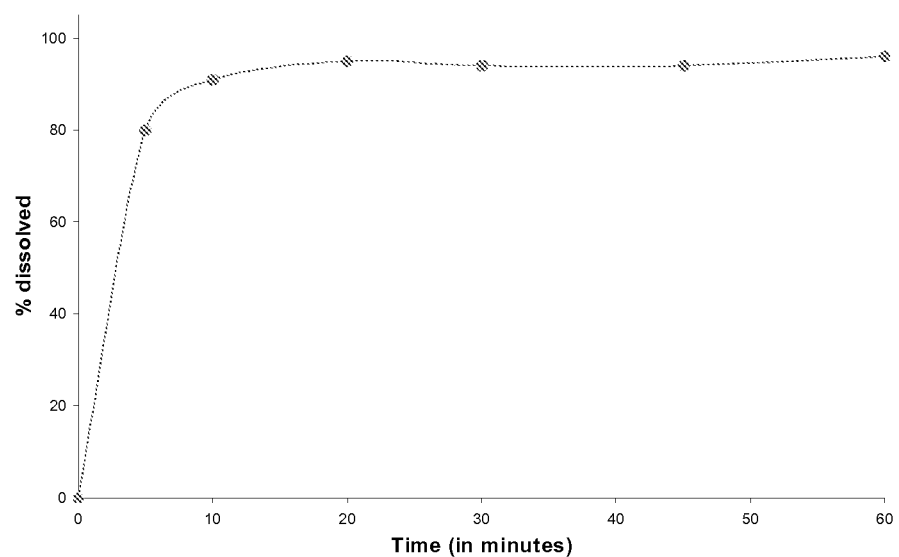

FIG. 2. Dissolution profile of a tablet comprising 30 mg ulipristal acetate, with the following excipients: lactose monohydrate 79 wt %, povidone 5 wt %, croscarmellose sodium 5 wt % and magnesium stearate 1 wt %.
X-axis: time in minutes
Y-axis: % dissolved composition

DETAILED DESCRIPTION OF THE INVENTION

The present invention relates to novel formulations of ulipristal acetate having improved properties. As disclosed above, the invention relates to oral tablets comprising ulipristal acetate combined with particular types and amounts of excipients, namely:
a diluent,
a binding agent,
croscarmellose sodium; and
magnesium stearate.

As illustrated in the experimental section, the selected excipients allow obtaining of granules having good processing properties (compressibility, flowability) and tablets with improved pharmacotechnical properties: good hardness range, low friability and rapid disintegration.

Proportions of Ingredients:
The tablets of this invention comprise:
ulipristal acetate in an amount of 3 to 18 wt %, preferably 5 to 15 wt %, even more preferably 8-12 wt %, together with the following excipients:
a diluent in an amount of 60 to 95 wt %, preferably 65 to 92 wt %, even more preferably 70-85 wt %;
a binding agent in an amount of 1 to 10 wt %, preferably 1.5 to 8.5 wt %, croscarmellose sodium in an amount of 1 to 10 wt %, preferably 1.5 to 8.5 wt %, and magnesium stearate in an amount of 0 to 5 wt %, preferably 0.5 to 4 wt %.

The term 'wt %' denotes an amount by weight, as a percentage of the total weight of the composition. The total percentage of the ingredients in a tablet adds up to 100.

In a preferred embodiment, the composition comprises from 5-15 wt % of ulipristal acetate, even more preferably from 8-12 wt %, more preferably about 10 wt %.

A preferred composition of this invention comprises:
ulipristal acetate in an amount of 5-15 wt %; preferably 8-12 wt %, more preferably about 10%,
a diluent in an amount of 65 to 92 wt %,
a binding agent in an amount of 1 to 10 wt %,
croscarmellose sodium in an amount of 1 to 10 wt %, and
magnesium stearate in an amount of 0.5 to 5 wt %,
the total of the percentage of the above ingredients in the tablet being 100.

In specific embodiments, Ulipristal acetate is used in a dosage of 1 to 50 mg per tablet, preferably 5 to 30 mg, particularly 10 or 30 mg.

As disclosed in the experimental section, these relative amounts lead to tablets that are adapted to provide improved properties for Ulipristal acetate. In particular, the results presented show that the use of a tablet vs a capsule improves bioavailability, and that the particular ratios of excipients and micronization as defined in the claims improves the dissolution profile.

The Diluent:

The diluent may be selected from any pharmaceutically acceptable agent or combination of agents that increases the bulk quantity of ulipristal acetate so that production of a compressed tablet of practical size is possible.

In a preferred embodiment, the diluent is selected from the group consisting of a monosaccharide, a disaccharide, a derivative polyol of a monosaccharide and hydrates thereof. The term 'derivative polyol of a monosaccharide' stands for a sugar alcohol such as mannitol, xylitol or sorbitol.

Preferably the diluent is selected from the group consisting of lactose monohydrate and mannitol. Indeed, studies were conducted by applicant to evaluate the effect of several distinct diluents on the tablet. Different batches were tested to assess the relative efficiency of the diluents. After addition of croscarmellose 5 wt % and magnesium stearate 1 wt %, compositions with lactose monohydrate or mannitol, 70 to 85 wt %, led to tablets with excellent appearance, compression and flowability properties.

In a most preferred embodiment, the diluent is lactose monohydrate is an amount of 65 to 92 wt %, more preferably 70-85 wt %.

The Binding Agent:

The binding agent, or binder, may be selected from any pharmaceutically acceptable agent (or combination of agents) which imparts cohesive qualities to powdered materials. The binding agent may be selected from starch, gelatin, sugars such as cellulose derivatives, and natural and synthetic gums may be used.

Advantageously, the binding agent of the tablet according to the invention is selected from the group consisting of polymers. The binding agent may be a natural polymer material such as polysaccharide, or a synthetic polymer such as a plastic polymer. Preferably, the binding agent is hydroxypropyl methyl cellulose and/or povidone.

Different tablets comprising 1 to 20 wt % of different binding agents (e.g., povidone, hydroxypropyl methyl cellulose or maize starch) were manufactured. Based on these tests, a relative amount of 1-10 wt % binding agent was retained as certain granules obtained with other amounts could not stand the drying step (formation of powder) and/or had lower dissolution profiles. Povidone or hydroxypropyl methyl cellulose gave the best results in that they enabled to obtain granules whatever diluents used (lactose monohydrate or mannitol at 70 to 85 wt %). Povidone is particularly preferred since very hard and homogeneous granules were obtained with povidone, which could easily stand the drying step.

Accordingly, in a preferred embodiment, the binding agent is or comprises povidone, preferably 1.5% to 8.5 wt % of povidone, even more preferably between 3-7 wt %, most preferably about 5 wt % povidone.

Croscarmellose Sodium:

The present tablets comprise croscarmellose sodium. Croscarmellose sodium is a disintegrant, e.g., facilitates break-up of the tablet. Croscarmellose sodium may be used alone or in combination with other disintegrants, preferably alone.

The experiments performed by applicant have shown that croscarmellose sodium, when used in combination with the other ingredients of the present invention, allows to reduce the disintegration time and to keep good pharmacotechnical characteristics when present in an amount of 1 to 10 wt %, preferably 1.5 to 8.5 wt %, and more preferably 4.5 to 5.5 wt %, or even more preferably about 5 wt %.

Magnesium Stearate:

In preferred embodiments, the tablets of the present invention contain magnesium stearate. Indeed, the inventors have shown that magnesium stearate is the most adapted lubricant to prevent adhesion to the tablet material to surfaces in the manufacturing process and to improve the flow characteristics of the powder material during manufacture of ulipristal acetate tablets.

While magnesium stearate may be used in combination with other lubricants, it is preferably used alone, in an amount comprised between 0.5 and 5 wt %.

Preferred Embodiments

Preferably, the tablet according to the present invention comprises lactose monohydrate as a diluent and povidone as a binding agent.

In a more specific embodiment, the tablet comprises: ulipristal acetate 5 to 15 wt %, lactose monohydrate 71 to 87 wt %, povidone 4.5 to 5.5 wt %, croscarmellose sodium 4.5 to 5.5 wt % and magnesium stearate 1 to 4 wt %, where the total percentage adds up to 100.

In an even more specific embodiment, the tablet comprises: ulipristal acetate 10%, lactose monohydrate 79 wt %, povidone 5 wt %, croscarmellose sodium 5 wt % and magnesium stearate 1 wt %.

The tablets can be prepared at a dosage of e.g., 10, 15, 20 or 30 mg ulipristal acetate.

Tabletting:

Tablets of the present invention may be prepared according to techniques known per se in the art. Suitable methods include direct compression ("dry blending"), dry granulation followed by compression, and wet granulation followed by drying and compression. Several methods include the use of compacting roller technology such as a chilsonator or drop roller, or molding, casting, or extrusion technologies. All of these methods are known per se in the art, and are described in detail in, for example, Lachman, et al., "The Theory and Practice of Industrial Pharmacy," Chapter 11, (3.sup.rd Ed. 1986), which is incorporated by reference herein. The tablet according to the invention can be a coated tablet or an uncoated tablet.

A preferred method for producing tablets of this invention is a wet granulation process. Indeed, the inventors have shown that such a method improves the qualities of the powder before compression and reduces the size of the tablet. More particularly, the wet granulation process led to better pharmacotechnical results on blends, an improvement of compressibility characteristics and a decrease of the final tablet mass.

An object of the present invention therefore resides in a method of manufacturing an ulipristal acetate tablet, the method comprising mixing the above ingredients and ulipristal acetate and forming a tablet. In a preferred embodiment, the tablet is formed be wet granulation.

The ingredients may be all mixed together simultaneously, or sequentially. In a typical embodiment, the diluent (e.g., lactose monohydrate), ulipristal acetate and the binding agent (e.g., povidone) are first mixed together, followed by addition of purified water. This granulation step is then followed by a drying step (e.g., in an oven at about 40° C., or on a fluidized air bed, or in a one-pot granulator). Optionally, a calibration step is then carried out, e.g., with a sieve comprised between about 600 and 850 µm, such as a 800 µm sieve or a 630 µm Frewitt sieve. Croscarmellose sodium and magnesium stearate are then added for the lubrication. The obtained formulation is then compressed to get the tablet (compression step). As a result of this process, croscarmellose (which is added after the granulation step) is in the external phase of the tablet, thereby allowing better disintegration and dissolution.

In the preparation of the tablets of this invention, commercial mixtures comprising diluents and binding agents may be used, such as Avicel® (microcrystalline cellulose), Starlac® (lactose monohydrate 85% with maize starch 15%) or, Ludipress® (lactose monohydrate 93% with Povidone 7%).

Therapeutic Applications:

The ulipristal acetate tablets of the invention are useful in a number of therapeutic indications, including contraception, including emergency contraception leiomyomata and hormonal diseases, such as hormone-responsive cancers.

Further aspects and advantages of the present invention will be disclosed in the following examples, which should be considered as illustrative and not limiting the scope of the present application.

EXAMPLES

Example 1

30 mg Ulipristal Acetate Tablet

A 30 mg ulipristal acetate tablet was prepared, containing the following ingredients:

| Ingredients | Quantity for one tablet (mg) | Quantity for one tablet (wt %) |
| --- | --- | --- |
| Ulipristal acetate | 30.00 | 10 |
| Lactose Monohydrate | 237.00 | 79 |
| Povidone | 15.00 | 5 |
| Croscarmellose sodium | 15.00 | 5 |
| Magnesium stearate | 3.00 | 1 |
| Total | 300.00 | 100 |

Lactose monohydrate 79 wt %, ulipristal acetate 10 wt % and povidone 5 wt % were mixed and purified water was added. This granulation step was immediately followed by a drying step in an oven at 40° C. Then, a calibration step with a Frewitt 630 µm sieve was carried out. Croscarmellose sodium 5 wt % and magnesium stearate 1 wt % were added for the lubrication step. The obtained formulation is compressed to get the tablet.

Example 2

Ulipristal Acetate Tablets

Further compositions of this invention contain the following ingredients:

| Ingredients | 10 mg tablet Quantity for one tablet in mg (wt %) | 30 mg tablet Quantity for one tablet in mg (wt %) |
| --- | --- | --- |
| Ulipristal acetate | 10.00 (10) | 30.00 (10) |
| Lactose Monohydrate | 79.00 (79) | 246.00 (82) |
| Povidone | 5.00 (5) | 9.00 (3) |
| Croscarmellose sodium | 5.00 (5) | 12.00 (4) |
| Magnesium stearate | 1.00 (1) | 3.00 (1) |
| Total | 100.00 (100) | 300.00 (100) |

Example 3

Reference 10 mg Ulipristal Acetate Tablet

A reference 10 mg ulipristal acetate tablet was prepared, following the method of example 2, containing the following ingredients:

| Ingredients | Quantity for one tablet (mg) | Quantity for one tablet (wt %) |
| --- | --- | --- |
| Ulipristal acetate | 10.00 | 6.7 |
| Mannitol | 41.00 | 27 |
| Microcrystalline cellulose | 91.00 | 61 |
| Croscarmellose sodium | 2.5 | 1.7 |
| Magnesium stearate | 1.5 | 1 |
| Talc | 4.0 | 2.6 |
| Total | 150.00 | 100 |

Example 4

Bioavailability Studies

A comparative bioavailability study of a 10 mg tablet vs different ulipristal acetate capsule formulations and a study characterizing the pharmacokinetic profile have been performed. Various assay methods have been employed in the measurement of ulipristal acetate in plasma or serum, including radioimmunoassay (RIA) and liquid chromatography with tandem mass spectrometry (LC-MS/MS). Because of the presence of cross-reacting metabolites, the RIA fails to distinguish the parent ulipristal acetate from potential cross-reactive metabolites present in the circulation, and results reported using this method hence represents the sum of ulipristal acetate and its cross-reactive metabolites. The LC-MS/MS has been developed for use in menopausal and non menopausal human plasma and serum, and permits separation and determination of both ulipristal acetate and its pharmacologically active metabolite, 17α-acetoxy-11β-[4-N-methy-lamino-phenyl)-19-norpregna-4,9-diene-3,20-dione.

The comparative bioavailability study also included a re-assay of samples using the non-selective RIA, thereby providing a point of reference to which results from other studies could be compared irrespective of the analytical method employed.

Comparative bioavailability studies were performed as a pharmacokinetic bridging study between different formulations of ulipristal acetate. The formulations tested included a 10 mg capsule with micronized ulipristal acetate in 120 mg microcrystalline cellulose, and a 10 mg ulipristal acetate tablet. The experiments were carried out to compare the bioavailability and the bioequivalence of ulipristal acetate, or of its metabolites, between these two formulations. As disclosed in Table 1 below, the best absorption profile was observed for the tablet formulation with the following PK parameters (mean±SD or range): Cmax: 56.7±29.1 ng/mL, tmax: 0.63 h (mean range: 0.50-2.00 h), $AUC_{0-t}$: 171.79±85.59 h·ng/mL.

The term '$C_{max}$' stands for a peak of ulipristal acetate concentration in the plasma. The term '$AUC_{0-t}$' denotes the area under the concentration time profile from 0 to time t. The term 'SD' refers to standard deviation.

TABLE 1

| Ulipristal acetate 10 mg | | $T_{max}$ (h) | $C_{max}$ (ng/ml) | $AUC_{0-t}$ (ng · h/ml) | $AUC_{0-\infty}$ (ng · h/ml) |
|---|---|---|---|---|---|
| Capsule | Mean | 1.13[1] | 35.0 | 170.58 | 193.37 |
| | Range | 0.5-3.00 | 15.0-64.1 | 53.4-291.9 | 62.9-315.4 |
| | SD | — | 20.0 | 84.18 | 96.93 |
| | CV (%) | 60 | 57 | 49 | 50 |
| Tablet | Mean | 0.63[1] | 56.7 | 171.79 | 189.86 |
| | Range | 0.50-2.00 | 20.7-94.5 | 74.3-291.7 | 85.7-340.7 |
| | SD | — | 29.1 | 85.59 | 99.90 |
| | CV (%) | 63 | 51 | 50 | 53 |

[1]Median

The results from comparative bioavailability studies also suggest that ulipristal acetate is absorbed faster and has a greater overall bioavailability for tablet compared with the capsule. Mean $C_{max}$ and $AUC_{0-t}$ for ulipristal acetate was in the best cases 95% and 40% higher, respectively, after administration of the tablet compared to the capsule (see FIG. 1). This trend was also reflected in a mean $C_{max}$ and $AUC_{0-t}$ for the active monodemethylated metabolite, 17α-acetoxy-11β-[4-N-methylamino-phenyl)-19-norpregna-4,9-diene-3,20-dione, that was 92% and 25% higher, respectively, for the tablet versus the capsule.

These results show that in comparison with the other formulation, the tablet formulation was absorbed faster, had a higher plasma concentration peak, and had a greater overall bioavailability as measured by the AUC measured in the study and extrapolated to infinity for the parent compound and metabolite.

These pharmacokinetic results demonstrate the advantages of the tablet form versus the capsule.

Example 5

Dissolution Profile for the Tablet According to Example 1

Dissolution studies were carried out using various tablets, including the tablet of example 1. The dissolution tests were conducted according to the general monograph of the European Pharmacopoeia § 2.9.3:
Paddle apparatus Dissolution medium: HCl 0.1N
Rotation speed: 50 rpm
Temperature: 37° C.±0.5° C.

The results depicted in FIG. 2 show that the tablets of this invention dissolve fully and rapidly.

Example 6

Comparative Dissolution Profiles

Table 2 presents the comparative dissolution profiles of the tablets of examples 1 and 3, which contain different ratio of ingredients. The results unexpectedly show that the tablet of Example 1, which is made in accordance with the present invention, has a much better dissolution profile than the reference tablet of example 3, illustrating the importance of the specific wt % of the invention for Ulipristal acetate formulation.

TABLE 2

Comparative dissolution profiles: ulipristal acetate dissolved (%) versus time (minutes)

| | Time (min) | | | | | | |
|---|---|---|---|---|---|---|---|
| | 0 | 5 | 10 | 20 | 30 | 45 | 60 |
| Ex 1 | 0 | 80 | 91 | 95 | 94 | 94 | 96 |
| Ex 3 | 0 | 71 | 83 | 89 | 91 | 93 | 93 |

The invention claimed is:
1. A pharmaceutical tablet for oral administration comprising:
   3 to 18 wt % of ulipristal acetate, wherein ulipristal acetate is present in the tablet in an amount ranging from 5 mg to 50 mg,
   60 to 95 wt % of a diluent selected from the group consisting, of lactose monohydrate and mannitol,
   1 to 10 wt % of a binding agent selected from the group consisting of hydroxypropyl methyl cellulose and povidone,
   1 to 10 wt % of croscarmellose sodium, and
   0 to 5 wt % magnesium stearate,
   wherein the tablet is an oral tablet and is uncoated,
   and wherein at least about 90% (w/w) of ulipristal acetate present in the tablet is dissolved within about 20 minutes when the tablet is subjected to an in vitro dissolution assay according to the general monograph of the European Pharmacopoeia §2.9.3, at 37°C.±0.5°C., a rotation speed of 50 rpm and pH=1.
2. The tablet of claim 1, wherein the dUuent is in an amount of 65 to 92 wt %.
3. The tablet of claim 1, wherein the binding agent is in an amount of 1.5 to 8.5 wt %.
4. The tablet of claim 1, wherein croscarmellose sodium is in an amount of 1.5 to 8.5 wt %.
5. The tablet of claim 1, wherein magnesium stearate is in an amount of 0.5 to 4 wt %.
6. The tablet according to claim comprising 10 wt % ulipristal acetate.
7. The tablet according to claim 1, comprising 5 to 30 mg ulipristal acetate.
8. The tablet according to claim 1, wherein the diluent is lactose monohydrate and the binding agent is povidone.
9. The tablet according to claim 1, comprising ulipristal acetate 6 to 12 wt %, lactose monohydrate 71 to 87 wt %, povidone 4.5 to 5.5 wt %, croscarmellose sodium 4.5 to 5.5 wt % and magnesium stearate 1 to 4 wt %.

10. The tablet of claim 9, comprising ulipristal acetate 10 wt %, lactose monohydrate 79 wt %, povidone 5 wt %, croscarmellose sodium 5 wt % and magnesium stearate 1 wt %.

11. A method of manufacturing the tablet according to claim 1, the method comprising mixing the ingredients and ulipristal acetate and forming a tablet.

12. The tablet of claim 1, comprising 5 mg ulipristal acetate.

13. The tablet of claim 1, comprising 10 mg ulipristal acetate.

14. The tablet of claim 1, comprising 15 mg ulipristal acetate.

15. The tablet of claim 1, comprising 20 mg ulipristal acetate.

16. The tablet of claim 1, comprising 30 mg ulipristal acetate.

* * * * *

UNITED STATES PATENT AND TRADEMARK OFFICE
CERTIFICATE OF CORRECTION

| | | |
|---|---|---|
| PATENT NO. | : 8,512,745 B2 | Page 1 of 1 |
| APPLICATION NO. | : 12/329865 | |
| DATED | : August 20, 2013 | |
| INVENTOR(S) | : Gainer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 541 days.

Signed and Sealed this
Seventeenth Day of February, 2015

Michelle K. Lee
*Deputy Director of the United States Patent and Trademark Office*